(12) United States Patent
Lim et al.

(10) Patent No.: US 9,364,550 B2
(45) Date of Patent: Jun. 14, 2016

(54) BIOACTIVE CARBON NANOTUBE COMPOSITE FUNCTIONALIZED WITH β-SHEET POLYPEPTIDE BLOCK COPOLYMER, AND PREPARATION METHOD THEREOF

(75) Inventors: Yong-Beom Lim, Seoul (KR); Woo-jin Jeong, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 14/239,426

(22) PCT Filed: Aug. 16, 2012

(86) PCT No.: PCT/KR2012/006502
§ 371 (c)(1),
(2), (4) Date: Feb. 18, 2014

(87) PCT Pub. No.: WO2013/025052
PCT Pub. Date: Feb. 21, 2013

(65) Prior Publication Data
US 2014/0206061 A1   Jul. 24, 2014

(30) Foreign Application Priority Data

Aug. 18, 2011   (KR) .................. 10-2011-0082003

(51) Int. Cl.
| | | |
|---|---|---|
| *A61K 38/00* | (2006.01) | |
| *A61K 47/48* | (2006.01) | |
| *C08K 3/04* | (2006.01) | |
| *C08L 89/00* | (2006.01) | |
| *C07K 7/08* | (2006.01) | |
| *C07K 17/02* | (2006.01) | |
| *C01B 31/02* | (2006.01) | |
| *G01N 33/551* | (2006.01) | |
| *G01N 33/58* | (2006.01) | |
| *B82Y 30/00* | (2011.01) | |
| *B82Y 40/00* | (2011.01) | |
| *C08L 77/04* | (2006.01) | |
| *C07K 14/00* | (2006.01) | |
| *B82Y 15/00* | (2011.01) | |
| *B82Y 5/00* | (2011.01) | |

(52) U.S. Cl.
CPC ..... *A61K 47/48023* (2013.01); *A61K 47/48869* (2013.01); *B82Y 30/00* (2013.01); *B82Y 40/00* (2013.01); *C01B 31/0273* (2013.01); *C07K 7/08* (2013.01); *C07K 14/00* (2013.01); *C07K 17/02* (2013.01); *C08K 3/04* (2013.01); *C08L 77/04* (2013.01); *C08L 89/00* (2013.01); *G01N 33/551* (2013.01); *G01N 33/587* (2013.01); *B82Y 5/00* (2013.01); *B82Y 15/00* (2013.01)

(58) Field of Classification Search
None
See application file for complete search history.

(56) References Cited

U.S. PATENT DOCUMENTS

| | | | | |
|---|---|---|---|---|
| 7,846,891 | B2 | 12/2010 | Ellis-Behnke | |
| 8,716,029 | B1 * | 5/2014 | Kim et al. | 436/501 |
| 2009/0208548 | A1 * | 8/2009 | Mason et al. | 424/405 |

FOREIGN PATENT DOCUMENTS

| | | |
|---|---|---|
| KR | 1020040075620 | 8/2004 |
| KR | 1006823810000 | 2/2007 |

OTHER PUBLICATIONS

Chi-Cheng, Chiu, et al., "Molecular dynamics study of a carbon nanotube binding reversible cyclic peptide." ACS NANO, Apr. 2010, vol. 4, No. 5, pp. 2539-2546.

* cited by examiner

*Primary Examiner* — Karlheinz R Skowronek
*Assistant Examiner* — Sergio Coffa
(74) *Attorney, Agent, or Firm* — Duane Morris LLP; J. Rodman Steele, Jr.; Gregory M. Lefkowitz

(57) ABSTRACT

The present invention relates to a bioactive carbon nanotube composite functionalized with a β-sheet polypeptide block copolymer by combination self-assembly, which shows excellent water dispersion, and has biological activity so as to be used as stimulus-responsive and adaptable biomaterials or in the manufacture of CNT-based electronic biosensor devices. In addition, the bioactive carbon nanotube composite can be used as a composition for delivery of a biological active material into cells. Further, the application of the interaction between a β-sheet peptide and a carbon-based hydrophobic material is expected to be useful for designing and developing an inhibitor for diseases caused by the abnormal folding of a protein and by biomacromolecular interactions (protein-protein, protein-DNA, and protein-RNA interactions etc).

15 Claims, 9 Drawing Sheets

Figure 5
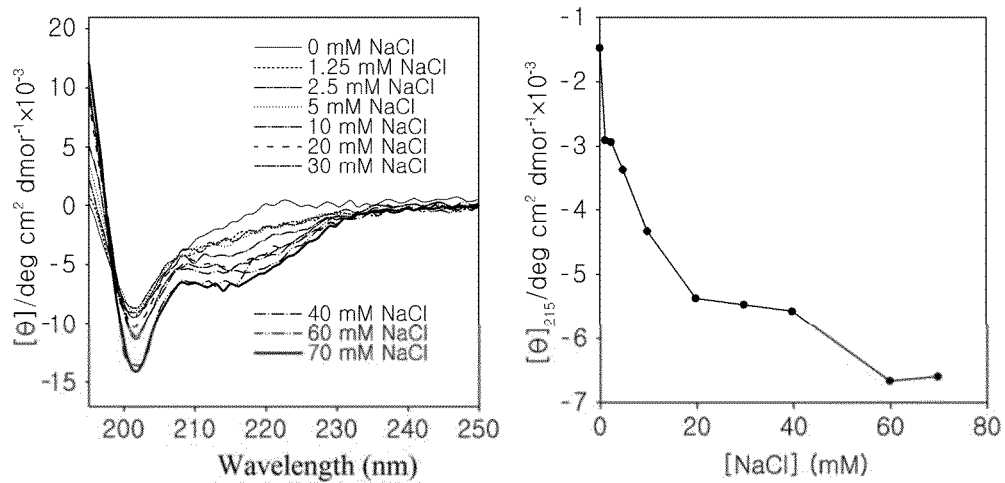
【Figure 6】
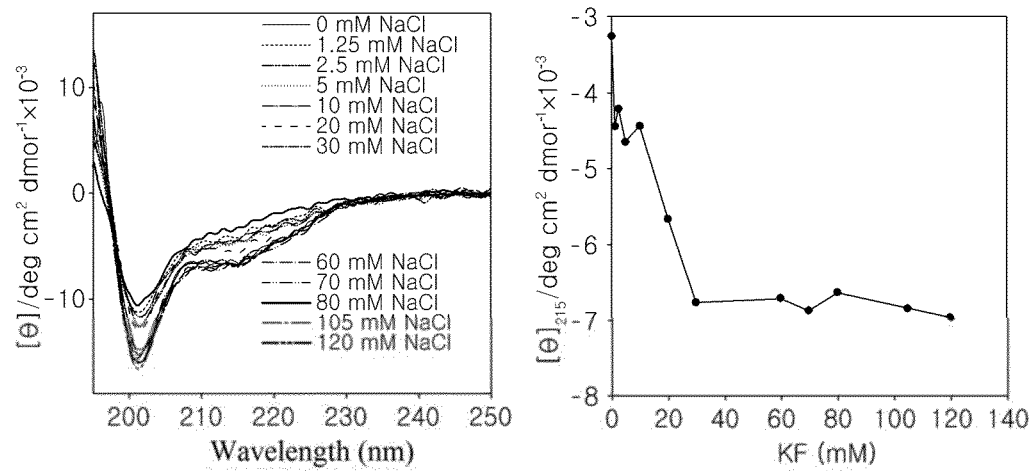

a) Mmt group removal
b) Cyclization

BIOACTIVE CARBON NANOTUBE COMPOSITE FUNCTIONALIZED WITH B-SHEET POLYPEPTIDE BLOCK COPOLYMER, AND PREPARATION METHOD THEREOF

CROSS-REFERENCE TO RELATED APPLICATIONS

This application is a §371 national stage entry of International Application No. PCT/KR2012/006502, filed Aug. 16, 2012, which claims priority to South Korean Patent Application No. 10-2011-0082003 filed Aug. 18, 2011, the entire contents of which are incorporated herein by reference.

TECHNICAL FIELD

The present invention relates to a bioactive carbon nanotube hybrid functionalized with β-sheet block copolypeptides. More specifically, the present invention relates to a highly water-dispersible, bioactive hybrid including carbon nanotubes functionalized with bioactive amphiphilic β-sheet block copolypeptides. The present invention also relates to a biosensor, inhibitors of protein misfolding diseases and biomacromolecular interactions, and a composition for intracellular delivery of a biologically active material using the carbon nanotube hybrid.

BACKGROUND ART

Carbon nanotubes (CNTs) are nanomaterials with a wide range of electronic, optical, mechanical, and biological applications. In order to use CNTs as biomaterials, a certain set of the physical, chemical and biological properties of CNTs needs to be satisfied. CNTs are intrinsically insoluble in aqueous solution and extensively bundled. Since biological systems are fundamentally composed of water-soluble molecules and structures, the solubilization of CNTs in aqueous solution is a prerequisite for their use in bioapplications. In addition, surface functionalization of CNTs with biologically active molecules is important in order to give them the capacity to execute specific biological functions.

The two main approaches for the solubilization of CNTs are based on covalent and non-covalent functionalization. In covalent functionalization, functional groups such as carboxylic acids or amines are formed by chemical reactions in defect sites of CNTs, which can then be used as sites for conjugation reactions with bioactive molecules. The problem with this approach is that it can damage the intrinsic structural and electrical properties of pristine CNTs. In contrast, the non-covalent approach can potentially preserve the π-conjugated system of the CNTs. This approach usually uses amphiphilic molecules, in which the hydrophobic part of the molecule wraps around the wall of the CNTs and hydrophilic part interacts with the aqueous solution. Various types of molecule, including low-molecular-weight amphiphiles or surfactants, polymers, and carbohydrates have been used for the non-covalent functionalization and solubilization of CNTs.

Korean Patent Publication No. 10-2004-0075620 describes non-covalent functionalization of carbon nanotubes in the state of solids to form carbon nanotube/nucleic acid complexes. Korean Patent Registration No. 10-0682381 describes carbon nanotube derivatives in which carbon nanotubes are non-covalently functionalized with egg white protein.

DISCLOSURE

Technical Problem

It is a first object of the present invention to provide a carbon nanotube hybrid functionalized with bioactive β-sheet block copolypeptides formed by conjugation of biologically active and hydrophilic peptide segments to β-sheet segments.

It is a second object of the present invention to provide a biosensor and a composition for intracellular delivery of a biologically active material utilizing the carbon nanotube hybrid functionalized with β-sheet block copolypeptides.

It is a third object of the present invention to provide a method for preparing the carbon nanotube hybrid functionalized with β-sheet block copolypeptides.

Technical Solution

In order to achieve the first object, the present invention provides a hybrid of β-sheet block copolypeptides and carbon nanotubes wherein each β-sheet block copolypeptide consists of a β-sheet polypeptide block and a bioactive polypeptide block, the β-sheet polypeptide block has an alternating series of nonpolar amino acids and polar amino acids or contains 50 to 100% of nonpolar amino acids, the bioactive polypeptide block consists of polar amino acids accounting for 50-100% of the total amino acids thereof, the β-sheet polypeptide block is non-covalently bound to the surface of the carbon nanotubes, and the bioactive polypeptide block is hydrophilic and exposed outside the hybrid.

According to one embodiment of the present invention, the nonpolar amino acids may be selected from phenylalanine, alanine, valine, isoleucine, leucine, methionine, tyrosine, and tryptophan.

According to one embodiment of the present invention, the polar amino acids may be selected from lysine, glycine, arginine, proline, glutamine, serine, histidine, aspartic acid, glutamic acid, threonine, aspargine, cysteine, and selenocysteine.

According to a further embodiment of the present invention, the nonpolar amino acid of the β-sheet polypeptide block may be phenylalanine or tryptophan, and the polar amino acid of the β-sheet polypeptide block may be lysine, glutamic acid or glycine.

According to a further embodiment of the present invention, the β-sheet polypeptide blocks self-assemble via β-sheet hydrogen bonds among the peptide strands, and the phenylalanine or tryptophan may be non-covalently bound to the surface of the carbon nanotubes via π-π stacking and hydrophobic interactions.

According to a further embodiment of the present invention, the β-sheet block copolypeptide may be a macrocyclic peptide in which the N- and C-termini are linked to each other.

In order to achieve the second object, the present invention provides a biosensor including the hybrid of β-sheet block copolypeptides and carbon nanotubes, and a ligand or receptor attached to the hybrid to react with a target biomaterial.

According to one embodiment of the present invention, the ligand or receptor may be selected from enzyme substrates, ligands, amino acids, peptides, proteins, enzymes, lipids, cofactors, carbohydrates, and combinations thereof.

The present invention also provides a composition for intracellular delivery of a biologically active material which includes, as an active ingredient, the hybrid of β-sheet block copolypeptides and carbon nanotubes.

In order to achieve the third object, the present invention provides a method for preparing a hybrid of β-sheet block copolypeptides and carbon nanotubes, the method including (a) removing a suspending solvent from a suspension of carbon nanotubes to obtain pretreated carbon nanotubes, and (b) adding the pretreated carbon nanotubes to an aqueous solution of β-sheet block copolypeptides to obtain a dispersion.

According to one embodiment of the present invention, the dispersion may further include a salt.

According to a further embodiment of the present invention, in step (a), the suspending solvent may be tetrahydrofuran and may be removed by centrifugation.

According to a further embodiment of the present invention, the salt may be present at a concentration of 1 mM or more in the dispersion and the dispersion may be prepared by sonication.

Advantageous Effects

The hybrid of the present invention is prepared by functionalizing carbon nanotubes with bioactive amphiphilic β-sheet block copolypeptides. The peptide/carbon nanotube hybrid is highly water dispersible and is bioactive. Due to these advantages, the peptide/carbon nanotube hybrid can be utilized as a stimuli-responsive biomaterial or to fabricate CNT-based electronic biosensor devices. In addition, the peptide/carbon nanotube hybrid can be applied to compositions for intracellular delivery of biologically active materials. Based on the interactions between the β-sheet peptides and the carbon-based hydrophobic materials, the peptide/carbon nanotube hybrid is expected to be useful in designing and developing inhibitors against protein-misfolding diseases.

DESCRIPTION OF DRAWINGS

FIG. 5 shows the influence of ionic strength on the formation of β-sheets of block copolypeptides: CD spectra measured at various salt concentrations (left) and a graph showing the molar ellipticities of depending on the content of β-sheets in β-sheet block copolypeptides, as measured at 215 nm (right).

FIG. 6 shows the influence of ionic strength on the formation of β-sheets of block copolypeptides: CD spectra measured at various salt concentrations (0-120 mM) (left) and a graph showing the molar ellipticities depending on the content of β-sheets in β-sheet block copolypeptides, as measured at 215 nm (right).

BEST MODE

Figure 1:
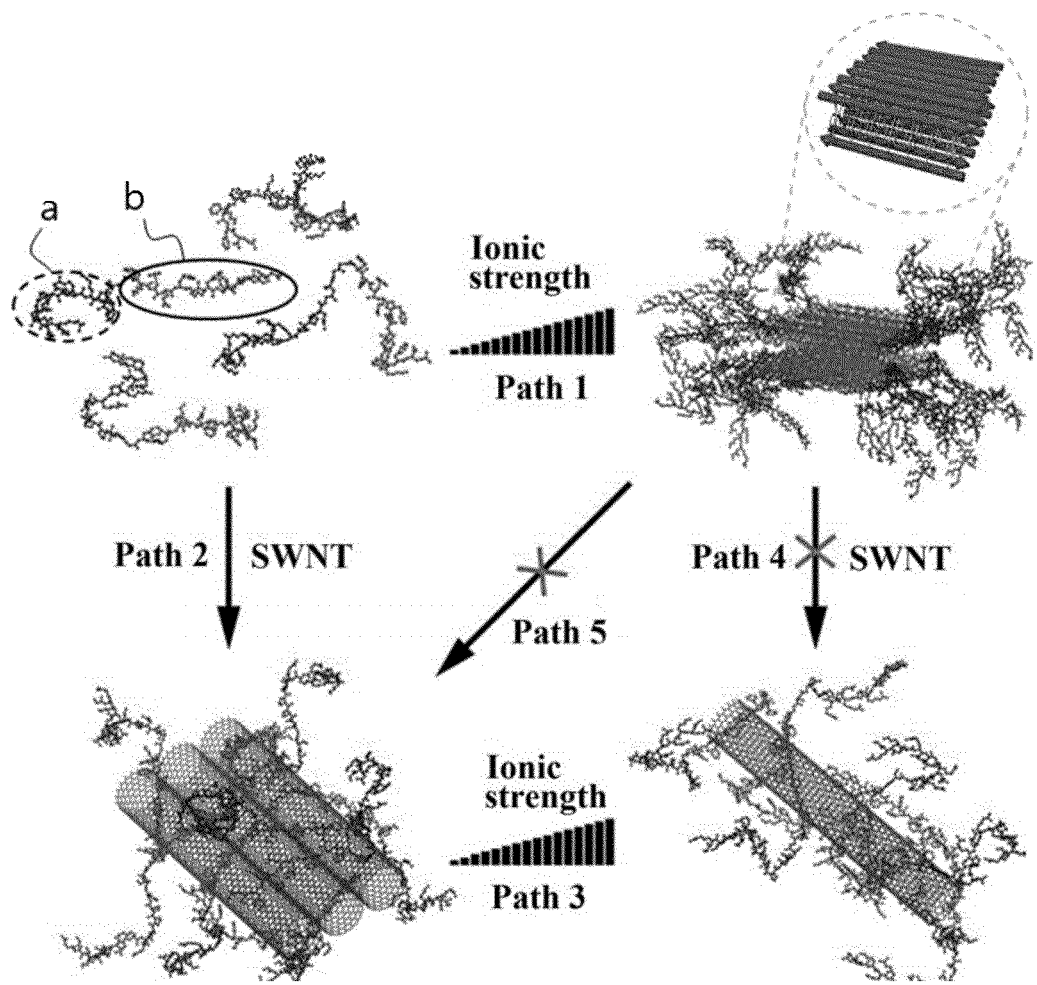
FIG. 1 is a conceptual diagram showing various reaction paths of combination self-assembly between β-sheet block copolypeptides and single-walled carbon nanotubes (SWCNTs) of a hybrid according to the present invention: a and b of the peptide represent a bioactive segment (GRKKRRQRRRPPQGSGG) and a β-sheet self-assembly segment (FKFEFKFEFKFE), respectively.

The present invention will now be described in more detail.

Peptides (the minimal form of proteins) can be developed as protein-like artificial nanomaterials when properly designed and self-assembled into controllable nanostructures.

Notably, self-assembling β-sheet peptides can be functionalized to become bioactive nanostructures when a biologically active and hydrophilic peptide segment is conjugated to the β-sheet segment, yielding bioactive β-sheet block copolypeptides. In doing so, diverse types of controllable and biologically useful β-sheet peptide nanostructures can be fabricated.

β-Sheet block copolypeptides can be self-assembled by themselves into nanostructures. In addition, control over the self-assembly of β-sheet block copolypeptides allows their co-assembly with carbon nanotubes instead of self-assembly.

The present invention provides a technique for preparing a β-sheet block copolypeptide/carbon nanotube hybrid based on co-assembly between β-sheet block copolypeptides and carbon nanotubes.

The present invention provides a bioactive carbon nanotube hybrid that is prepared by combination self-assembly of bioactive β-sheet block copolypeptides with CNTs.

The present invention provides a water-soluble hybrid including carbon nanotubes and a plurality of β-sheet block copolypeptides wherein each β-sheet block copolypeptide is prepared by copolymerization of a bioactive polypeptide segment and a β-sheet polypeptide segment and completely or partially wraps around the surface of the carbon nanotubes by non-covalent binding, the β-sheet polypeptide segment is bound to the surface of the carbon nanotubes, the hydrophilic polypeptide segment is charged and exposed to the outer surface layer, the bioactive polypeptide block has an alternating arrangement of one or more kinds of amino acids selected from lysine, glycine, arginine, proline, glutamine, and serine, and the β-sheet polypeptide has an alternating arrangement of one or more kinds of amino acids selected from phenylalanine, tryptophan, lysine, glutamic acid, and glycine.

The β-sheet block copolypeptide is a linear peptide or a macrocyclic peptide in which the N- and C-termini are linked to each other.

The self-assembly system of the present invention should include force-balance processes between two classes of competing forces: the attractive forces between the β-sheet segments, and the attractive forces between the β-sheet segments and the CNTs. If the former predominates, the peptides should take part in the formation of β-sheet nanostructures while the CNTs are still insoluble in aqueous solution. On the other hand, water-soluble/bioactive CNTs that are non-covalently functionalized with bioactive β-sheet block copolypeptides can be constructed if the latter attractive forces become dominant. More detailed understanding of such force-balance processes is valuable for controlling and thereby inhibiting the aggregation behavior of β-amyloids and related proteins in protein-misfolding diseases.

The β-sheet polypeptides self-assemble via β-sheet hydrogen bonds among the peptide strands, and phenylalanine or tryptophan residues of the β-sheet polypeptides are bound to the surface of the carbon nanotubes via π-π stacking interactions.

As demonstrated above, the two segments of the β-sheet block copolypeptides have markedly different properties with regard to polarity and aggregation propensity.

The bioactive segment (for example, a in FIG. 1) is based on Tat cell-penetrating peptide. Since this segment contains multiple lysines and arginines, it becomes highly charged and polar in aqueous solution. The self-assembly segment has an alternating series of nonpolar (phenylalanine or tryptophan) and polar (lysine and glutamic acid) amino acids, which promotes the formation of β-sheet hydrogen bonds among the peptide strands. The block copolypeptide of such an arrangement can form β-sheet nanoribbon structures only at a sufficiently high ionic strength due to the bulkiness and the multiple positive charges of the hydrophilic segment (path 1 in FIG. 1). In the absence of salt or at a low ionic strength, the block copolypeptides exist mostly in random-coil conformations.

The present invention provides a biosensor including the water-soluble hybrid of β-sheet block copolypeptides and carbon nanotubes, and a ligand or receptor attached to the hybrid to react with a target biomaterial.

In the present invention, the target biomaterial is a material that can serve as a target detected as a result of a reaction with the ligand or receptor. The target biomaterial is preferably selected from proteins, nucleic acids, antibodies, enzymes, carbohydrates, lipids, and other biomolecules, and is more preferably a disease-related protein, nucleic acid or carbohydrate.

In the present invention, the ligand or receptor may be an enzyme substrate, a ligand, an amino acid, a peptide, a protein, an enzyme, a lipid, a cofactor or a carbohydrate.

The present invention also provides a composition for intracellular delivery of a biologically active material which includes the β-sheet block copolypeptide-carbon nanotube hybrid as an active ingredient.

The composition of the present invention can penetrate the cell membrane and directly act within the cell. In contrast, general biologically active materials do not readily cross the cell membrane. Accordingly, the composition of the present invention can provide a significant breakthrough in the development of drug delivery systems.

The composition of the present invention includes 0.0001 to 50% by weight of the active ingredient, based on the total weight thereof.

The composition of the present invention may further contain one or more active ingredients that exhibit functions identical or similar to those of the β-sheet block copolypeptide-carbon nanotube hybrid.

For administration, the composition of the present invention may further include one or more pharmaceutically acceptable carriers in addition to the active ingredients described above. Suitable pharmaceutically acceptable carriers include physiological saline, sterile water, Ringer's solution, buffered saline, dextrose solution, maltodextrin solution, glycerol, ethanol, liposome, and mixtures thereof. If necessary, the composition of the present invention may further include one or more additives selected from those well known in the art, for example, antioxidants, buffer solutions, and bacteriostatic agents. The composition of the present invention may be formulated with diluents, dispersants, surfactants, binders and lubricants to prepare injectables, such as aqueous solutions, suspensions or emulsions, pills, capsules, granules or tablets. Target organ-specific antibodies or other ligands may be bound to the carriers. Furthermore, the composition of the present invention may be formulated depending on the type of disease or the kind of ingredient by suitable techniques known in the art.

The composition including the hybrid as an active ingredient may be delivered intracellularly via suitable routes, including intravein, intraperitoneal, intramuscular, subcutaneous, intradermal, nasal, mucosal, inhalation and oral routes. The dosage may vary depending on the body weight, age, sex, health and diet of subjects to be treated, the time and mode of administration, the rate of excretion, the severity of disease, and other relevant factors. A daily dose of the hybrid may range from about 0.1 to about 100 mg/kg, preferably 0.5 to 10 mg/kg, and is more preferably administered in a single dose or divided doses.

The present invention provides a method for preparing a water-soluble hybrid of β-sheet block copolypeptides and carbon nanotubes, the method including (a) suspending carbon nanotubes in tetrahydrofuran and evaporating the tetrahydrofuran by centrifugation to obtain pretreated carbon nanotubes, and (b) mixing the pretreated carbon nanotubes, a 5-200 µM aqueous solution of β-sheet block copolypeptides, and a 10-150 mM aqueous solution of sodium chloride, and sonicating the mixture.

The β-sheet block copolypeptide is a block copolymer of a bioactive polypeptide and a β-sheet polypeptide. The bioactive polypeptide has an alternating arrangement of one or more kinds of amino acids selected from lysine, glycine, arginine, proline, glutamine and serine, and the β-sheet polypeptide has an alternating arrangement of one or more kinds of amino acids selected from phenylalanine, tryptophan, lysine, glutamic acid and glycine.

The present invention will be explained with reference to the following examples. However, it will be evident to those skilled in the art that these examples are provided for illustrative purposes only and are not intended to limit the scope of the invention.

[Mode For Invention]

Fmoc-amino acids were purchased from Novabiochem (Germany). Fmoc-21-amino-4,7,10,13,16,19-hexaoxaheneicosanoic acid (Fmoc-NH-PEG5-COOH) and N-(Fmoc-8-amino-3,6-dioxaoctyl)succinamic acid (Fmoc-PEG2-Suc-OH or Fmoc-Ebes-OH) were purchased from Merck (Germany) and Anaspec (USA), respectively. Single-walled carbon nanotubes (ASP-100F, "purified" grade) produced by arc discharge were purchased from Hanwha Nanotec (Korea). Tissue-culture reagents were purchased from Invitrogen (USA).

SYNTHESIS EXAMPLE 1

Linear β-Sheet Block Copolypeptide (1) The peptide was synthesized on Rink Amide MBHA resin LL (Novabiochem) using standard Fmoc protocols, using a Tribute™ peptide synthesizer (Protein Technologies, Inc). Standard amino acid protecting groups were employed for the synthesis. The sequence of the β-sheet block copolypeptide was as follows:

Gly-Arg-Lys-Lys-Arg-Arg-Glu-Arg-Arg-Arg-Pro-Pro-Glu-Ser-Gly-Gly-Phe-

Lys-Phe-Glu-Phe-Lys-Phe-Glu-Phe-Lys-Phe-Glu
or

GRKKRRQRRRPPQGSGGFKFEFKFEFKFE (2) For the synthesis of the peptide with a fluorescent label at the N-terminus, a solution of 5-carboxyfluorescein (5 equivalent), HBTU (4.5 equivalent) and DIPEA (10 equivalent) in 1 mL of N-methyl-2-pyrrolidone (NMP) was added to the resin-bound peptide and reacted overnight. The resin was then successively washed with NMP and acetonitrile and dried in vacuo. The dried resin was treated with a cleavage solution (TFA:TIS:water=95:2.5:2.5) for 3 h and was triturated with t-butyl methyl ether. The peptides were purified by reverse-phase HPLC (water-acetonitrile, 0.1% TFA). The molecular weight was confirmed by MALDI-TOF mass spectrometry. The purity of the peptides was >95%, as determined by analytical HPLC.

The concentration was determined spectrophotometrically in water:acetonitrile (1:1) using the molar extinction coefficient of phenylalanine (195 mol$^{-1}$ cm$^{-1}$) at 257.5 nm.

EXPERIMENTAL EXAMPLES

Linear β-Sheet Polypeptide Block (1) Circular Dichroism (CD)

CD spectra were measured using a Chirascan™ circular dichroism spectrometer equipped with a Peltier temperature controller (Applied Photophysics., Ltd.). The spectra were recorded from 250 nm to 190 nm using a 2 mm path-length cuvette. Scans were repeated five times and averaged. The molar ellipticity was calculated per amino acid residue. Before measurement, 5 μM solutions of peptides with and without SWCNTs were incubated for 12 h in 20 mM or 60 mM NaCl at room temperature.

(2) Transmission Electron Microscopy (TEM)

2 mL samples were placed onto a carbon-coated copper grid and dried completely. 2 mL of water was added for 1 min to dissolve and remove any unbound peptide and was then wicked off using filter paper. The specimens were observed using a JEOL-JEM 2010 instrument operating at 150 kV. The obtained data were analyzed with Digital Micrograph™ software.

(3) Dynamic Light Scattering (DLS)

DLS experiments were performed at room temperature using an ALV/CGS-3 compact goniometer system equipped with a He—Ne laser operating at 632.8 nm. The detector optics employed optical fibers coupled to an ALV/SO-SIPD/DUAL detection unit, which employed an EMI PM-28B power supply and an ALV/PM-PD preamplifier/discriminator. The signal analyzer was an ALV5000/E/WIN multiple-tau digital correlator with 288 exponentially spaced channels. The scattering angle was 90°. The size distribution was determined using a constrained-regularization method.

(4) Fluorescence Spectroscopy

Steady-state fluorescence spectra were recorded using a Hitachi F-4500 fluorescence spectrophotometer and 1-cm path-length quartz cuvettes. The peptide concentration was typically 5 mM in a 50 mM NaCl solution. In order to measure the fluorescence from the phenylalanine residues, the samples were excited at 257 nm. Excitation and emission slits with a nominal band-path of 10 nm were used for the measurements.

(5) Tissue-Culture and Intracellular-Delivery Experiments

For microscopic observation of intracellular delivery of the β-sheet block copolypeptide/SWCNT hybrid, HeLa cells (4×10$^5$) were seeded on an 8-well Lab-tek II chambered cover-glass system (Nunc) in DMEM with 10% FBS and cultured overnight at 37° C. The cells were washed with DPBS and treated with the peptide/SWCNT hybrid for 20 min. Then, the sample solution was removed and the cells were further incubated for 90 min in DMEM. Before image acquisition, LysoTracker Red DND-99 (Invitrogen) was added at 50 nM for 5 min. A Nikon Eclipse TE2000-U inverted microscope equipped with argon (488 nm) and helium-neon (543 nm) lasers was used for the confocal images.

Experimental Example 1

Figure 2:
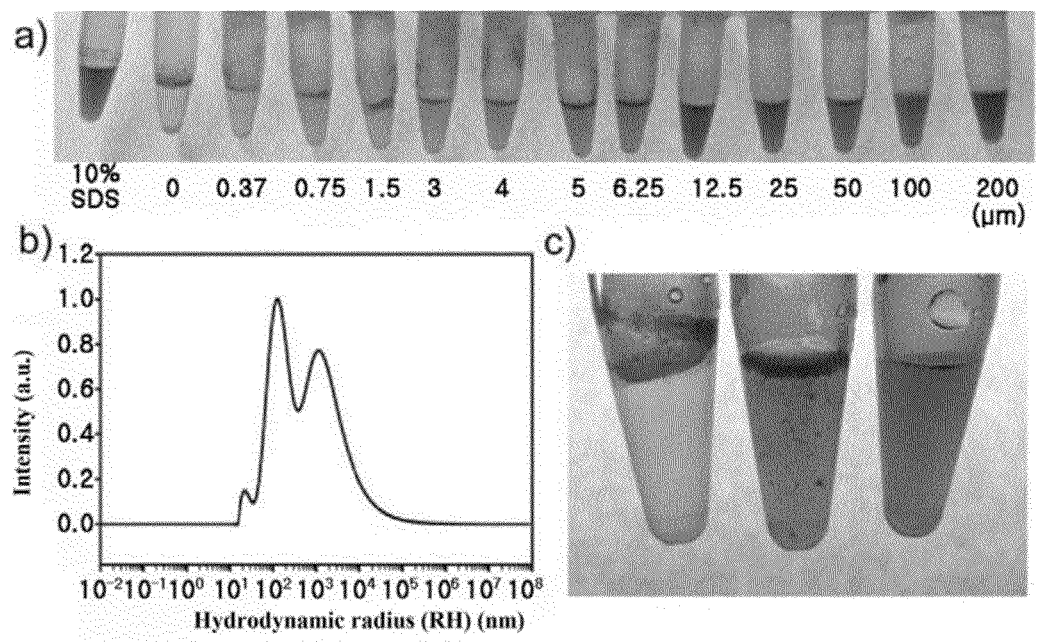
FIG. 2 shows solubilization of SWCNTs in pure water: a) images showing the influence of β-sheet block copolypeptide concentration on the solubilizations of the SWCNTs (the numbers represent the concentrations of the peptide), b) a graph showing distribution of the hydrodynamic radius ($R_H$) of the solubilized peptide/SWCNT hybrids as measured by dynamic light scattering (DLS), and c) images showing the influence of the β-sheet block copolypeptide concentration on the solubilization of the SWCNTs (the amount of SWCNTs was 5 μg) at peptide concentrations of 1.5, 5, and 12.5 μM from left to right.

First, it was confirmed whether this potential β-sheet forming peptide can bind to and then solubilize SWCNTs in pure water. The arc-produced SWCNTs were suspended in tetrahydrofuran (THF) and equal amounts of the SWCNTs (5 μg) were added into microcentrifuge tubes. After THF evaporation, the block copolypeptide solution (0.3 mL) was added and the mixture was subjected to sonication at room temperature for 15 min. As shown in a) and b) of FIG. 2, the SWCNTs became solubilized as the concentration of the peptide increased; most of the SWCNTs were suspended at a peptide concentration of around 12.5 μM (see c) of FIG. 2). This result suggests that phenylalanine residues in the block copolypeptide bind to the SWCNTs via hydrophobic and π-π stacking interactions, and the lysine and arginine-rich hydrophilic segment helps the dissolution of the peptide/SWCNT hybrids by interacting with the aqueous solution (FIG. 1). Zeta-potential (ζ) measurements showed that the peptide/SWCNT hybrids had large positive values (+58±3 mV), demonstrating the formation of a positively charged surface due to the exposure of the cationic and hydrophilic segments at the outer layer of the peptide/SWCNT hybrid.

Experimental Example 2

Next, the influence of ionic strength on the peptide/SWCNT hybrid formation was investigated. The β-sheet contents of the block copolypeptide solution increased with increasing NaCl concentration, and the increase reached a plateau at a salt concentration of around 50-60 mM (see FIG. 5). Based on this result, the influence of the ionic strength on the solubilization of the SWCNTs was investigated. This experiment was conducted at a peptide concentration of 5 μM, which was found to be insufficient to solubilize 5 μg of SWCNTs in pure water (the middle image in c) of FIG. 2).

Figure 3:
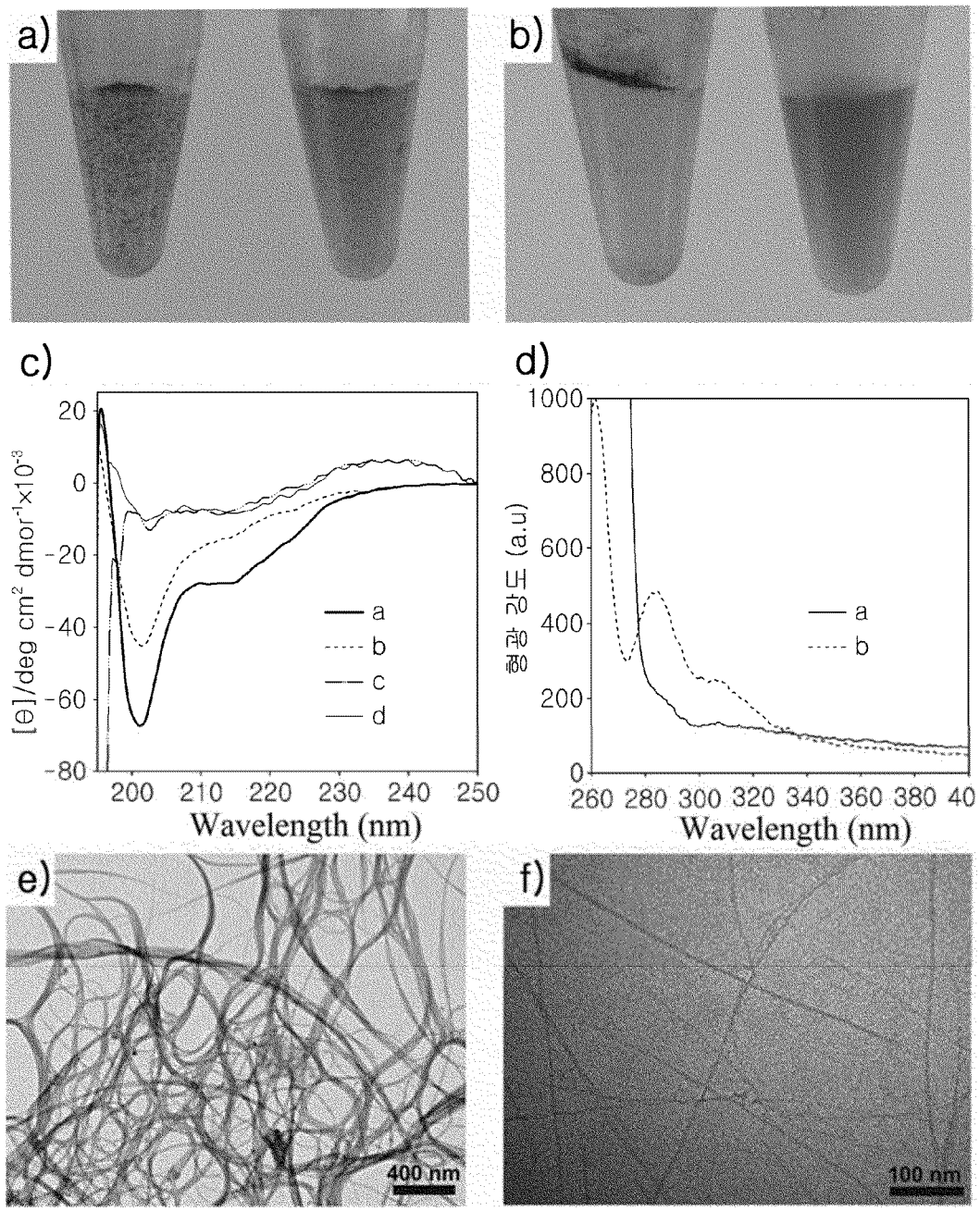
FIG. 3 shows the influence of ionic strength on the combination self-assembly of β-sheet peptide and SWCNTs: a) images of peptide samples subjected to a vortex in pure water (left) or in 50 mM NaCl (right), b) images of sonicated peptide samples in pure water (left) and 50 mM NaCl (right), c) circular dichroism (CD) spectra, a (bold solid line, 5 μM peptide+60 mM NaCl), b (dotted line, 5 μM peptide+20 mM NaCl), c (alternate long and two short dashes line, 5 μM peptide+60 mM NaCl+5 μg SWCNT), and d (fine solid line, 5 mM peptide+20 mM NaCl+5 μg SWCNTs), d) fluorescence emission spectra of peptide alone (b, dotted line) and peptide/SWCNT hybrid (a, solid line), and e) and f) TEM images of solubilized peptide/SWCNT (50 μM/5 μg) hybrids in pure water є and 20 mM NaCl (f).

As shown in a) of FIG. 3 (left), the peptide (5 μM) and SWCNT mixture in pure water revealed the presence of large granules of SWCNTs, indicating their incomplete solubilization. In contrast, the granules became smaller when salt was added (50 mM) and the solution was subjected to a vortex (the right image in a) of FIG. 3). Upon sonication of both mixtures, a significant difference was evident. The mixture in pure water showed the formation of largely insoluble SWCNT aggregates at the air-water interface (the left image in b) of FIG. 3), while the SWCNTs were almost completely solubilized in the presence of salt (the right image in b) of FIG. 3).

Therefore, the results demonstrate the enhancement in SWCNT solubilization at a high ionic strength. Considering that the block copolypeptide forms stable β-sheet nanoribbon structures at a salt concentration of 50 mM (FIG. 5), this behavior indicates that the attractive forces between the β-sheet segments and the SWCNTs are stronger than the attractive forces between the β-sheet segments and that the peptide/SWCNT combination self-assembly process is faster than the β-sheet formation. This was also supported by CD spectrum results recorded for the peptide and the peptide/SWCNT hybrid. The presence of the SWCNTs prevented the formation of the β-sheets, as manifested by the dramatic decrease in the negative minimum of ellipticity at 215 nm (see c) of FIG. 3). The strong attraction between the β-sheet segments and the SWCNTs, and the direct binding of the peptide on the SWCNTs were further confirmed by the disappearance of the phenylalanine fluorescence upon hybrid formation (see d) of FIG. 3).

Experimental Example 3

The TEM images revealed the influence of ionic strength on the formation of the peptide/SWCNT hybrid more dramatically.

Although the SWCNTs appeared well dispersed in a stable state in pure water, it was confirmed that the prepared hybrids could also show bundling of the SWCNTs under certain conditions (see e) of FIG. 3 and path 2 in FIG. 1). In contrast to this, most of the SWCNTs were unbundled when the hybrids were prepared in the presence of salt (see f) of FIG. 3 and path 3 in FIG. 1).

Thus, the findings imply that the presence of salt further strengthens the hydrophobic interactions between the phenylalanine and the SWCNTs, and screens non-specific charge interactions between the peptides, contributing to the efficient solubilization and unbundling of the SWCNTs.

Experimental Example 4

An investigation was made as to whether preassembled β-sheet nanoribbons could be disintegrated and used to solubilize CNTs in the presence of SWCNTs (path 4 or path 5 in FIG. 1).

As a result, even after extensive sonfication, it was revealed that the SWCNTs could not be solubilized and functionalized with the peptides once the β-sheet nanoribbons had formed.

Taken together, the results of the above experimental examples delineate two important findings during the combination self-assembly of β-sheet peptides and CNTs.

Firstly, when the associations between the β-sheet peptides are weak or the peptides are at the initial stage of self-assembly, the combination of path 2 and path 3 in FIG. 1 enables the fabrication of β-sheet block copolypeptide functionalized with bioactive CNTs.

Secondly, the results have implications for the inhibition of amyloid-fibril formation in protein-misfolding diseases. That is, allotropes of carbon (such as CNTs and fullerenes) might prevent amyloid formation. Given the difficulty of disintegrating preassembled β-sheet nanoribbons (path 4 and path 5), the primary targets for the carbon-based amyloid inhibitors should be the intermediate assemblies, such as the protofibrillar species that are formed during the early stages of amyloid fibril formation.

Experimental Example 5

In order to explore the possibility of using the peptide/SWCNT hybrids prepared by path 3 as cellular-delivery materials, the interaction of the hybrids with mammalian cells was investigated.

Since the hybrids were decorated with Tat cell-penetrating peptide, they were likely to enter into the cells efficiently. Tat cell-penetrating peptide (CPP) has been shown to cross the cytoplasmic and nuclear membrane barriers of cells. In order to visualize the hybrids, the peptide labeled with fluorescein was mixed with the unlabeled peptide at a 1:50 molar ratio, and the peptide mixture was used to functionalize SWCNTs. As shown in a) of FIG. 4, the hybrids become widely distributed throughout the cytoplasm, indicating efficient intracellular delivery of the hybrids.

Figure 4:
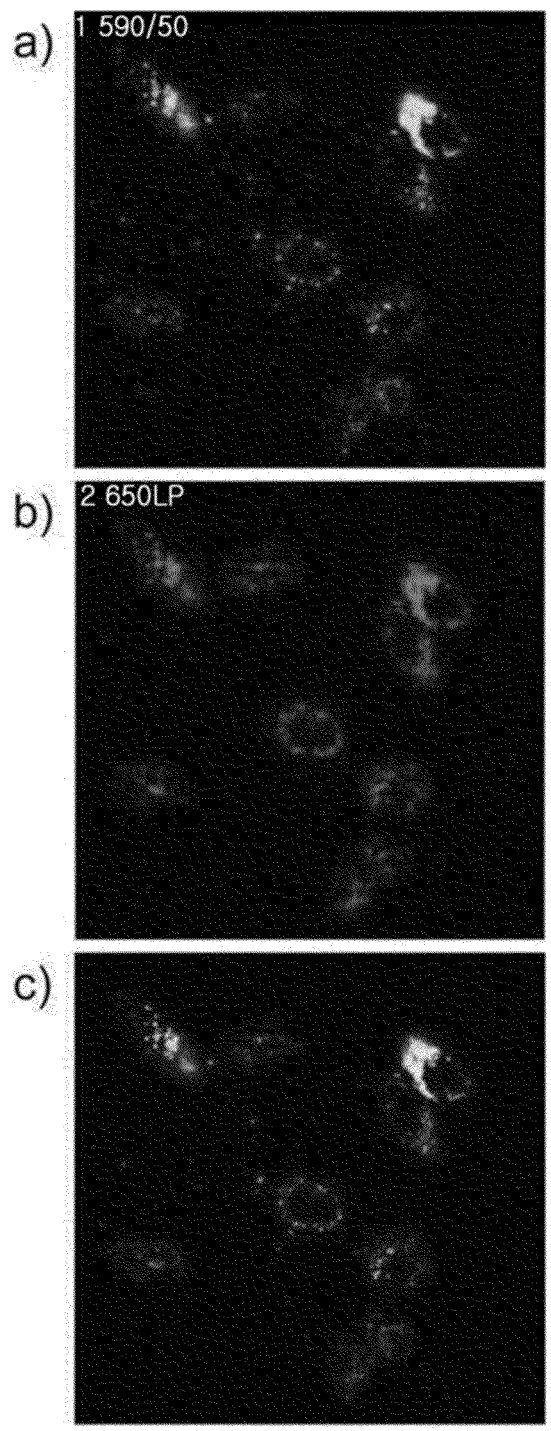
FIG. 4 shows images confirming intercellular delivery of peptide/SWCNT hybrids in HeLa cells: a) an image showing intracellular distribution of the peptide/SWCNT hybrids, b) an image showing cells stained with LysoTracker Red DND-99, and c) a merged image (magnification 400×).

The green fluorescence from the hybrids and the red fluorescence of the LysoTracker (a probe for labeling acidic organelles in live cells) indicate that the hybrids enter the cells by an endocytosis mechanism (see c) of FIG. 4). As an isolated peptide, Tat peptide can enter into the nucleus and nucleolus as well as the cytoplasm. However, the predominant localization of the hybrids in the cytoplasm, despite the nucleus localization activity of the Tat peptide, suggests that the hybrids cannot pass through the nuclear pore complex (NPC) because of their large size. Therefore, the result implies that the peptide is still in the SWCNT-bound state within the cells, demonstrating the stability of the hybrid.

SYNTHESIS EXAMPLE 2

Cyclic β-Sheet Block Copolypeptides (1) The peptides were synthesized on Rink Amide MBHA resin LL (Novabiochem) using standard Fmoc protocols, using a Tribute™ peptide synthesizer (Protein Technologies, Inc). For the synthesis, standard amino acid protecting groups were employed for the amino acids other than methoxytrityl (Mmt)-protected cysteine. The sequences of the β-sheet block copolypeptides (Peptides 1-4) were as follows:

```
1. cyclo[-Phe-Lys-Phe-Glu-Phe-Lys-Phe-Glu-Phe-PEG5-Thr-Arg-Gln-Ala-

Arg-Arg-Asn-Arg-Arg-Arg-Arg-Trp-Arg-Arg-PEG5-Cys-]
or cyclo[-FKFEFKFEF-PEG5-TRQARRNRRRRWRR-PEG5-C-]

2. cyclo[-Trp-Lys-Trp-Glu-Trp-Lys-Trp-Glu-Trp-Lys-Trp-Glu-Trp-Ebes-Gly-

Thr-Arg-Gln-Ala-Arg-Arg-Asn-Arg-Arg-Arg-Trp-Arg-Arg-Ebes-Cys-]
or cyclo [-WKWEWKWEWKWEW-Ebes-GTRQARRNRRRRWRR-Ebes-C-]

3. cyclo[-Trp-Trp-Gly-Trp-Trp-Ebes-Thr-Arg-Gln-Ala-Arg-Arg-Asn-Arg-Arg-

Arg-Arg-Trp-Arg-Arg-Ebes-]
or cyclo [-WWGWW-Ebes-TRQARRNRRRRWRR-Ebes-]

4. cyclo[-Gly-Trp-Trp-Trp-Trp-Ebes-Thr-Arg-Gln-Ala-Arg-Arg-Asn-Arg-Arg-

Arg-Arg-Trp-Arg-Arg-Ebes-]
or cyclo [-GWWWW-Ebes-TRQARRNRRRRWRR-Ebes-]
```

Figure 7:
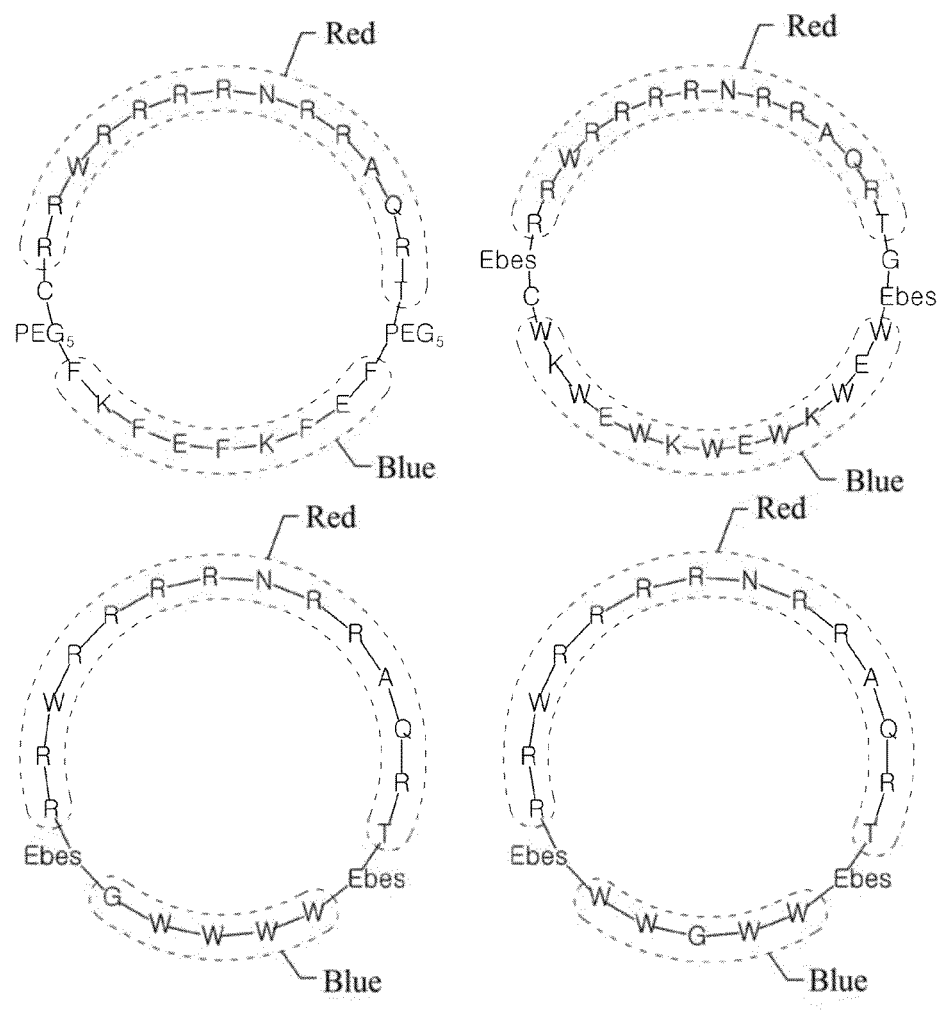
FIG. 7 shows the structures of cyclic β-sheet block copolypeptides (Peptides 1 to 4 of Synthesis Example 2) of hydrides according to the present invention.
Figure 13:
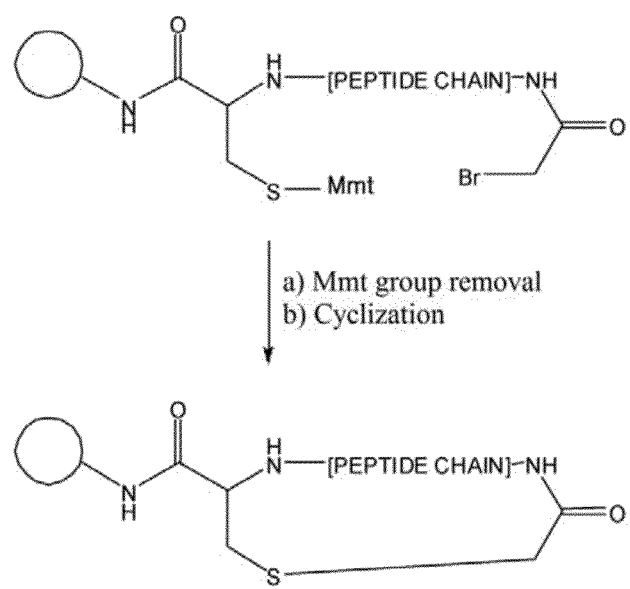
FIG. 13 depicts a cyclization reaction for the synthesis of a cyclic β-sheet block copolypeptide.

The block copolypeptides are macrocyclic peptides in which the N- and C-termini are linked through the cyclization reaction depicted in FIG. 13. The structures are shown in FIG. 7 (bioactive peptide segments and β-sheet self-assembly segments are indicated by "blue" and "red", respectively).

(2) The synthesized β-sheet block copolypeptides were cyclized by the following procedure. First, bromoacetic acid was coupled to the N-terminal of the resin-bound peptide, and a mixture of bromoacetic acid (20 equivalent) and (N,N'-diisopropylcarbodiimide (DIPC) incubated for 10 min for caboxylation was added to the resin. The resin was then washed with NMP and DCM, and a 1% TFA solution in DCM was added to the resin several times for 1 min to remove the Mmt groups from the cysteine. Thereafter, 3 mL of 1% DIPEA was added and the mixture was allowed to react at room temperature overnight for intramolecular cyclization. The resin was then successively washed with NMP and acetonitrile and dried in vacuo. The dried resin was treated with a cleavage solution (TFA:TIS:water=95:2.5:2.5) for 3 h and was triturated with t-butyl methyl ether. The peptides were purified by reverse-phase HPLC (water-acetonitrile, 0.1% TFA).

The molecular weight was confirmed by MALDI-TOF mass spectrometry. The purity of the peptides was >95%, as determined by analytical HPLC.

The concentrations of peptide 1 and peptide 2 were determined spectrophotometrically in water:acetonitrile (1:1) using the molar extinction coefficients of tryptophan at 280 nm and phenylalanine (195 $mol^{-1}cm^{-1}$) at 257.5 nm, respectively.

Experimental Examples

Cyclic β-Sheet Polypeptide Block (1) Transmission Electron Microscopy (TEM)

2 μL samples were placed onto a carbon-coated copper grid and dried completely. 2 μL of water was added for 1 min to dissolve and remove any unbound peptide and was then wicked off using filter paper. The specimens were observed using a JEOL-JEM 2010 instrument operating at 150 kV. The obtained data were analyzed with Digital Micrograph™ software.

(2) Circular Dichroism (CD)

CD spectra were measured using a Chirascan™ circular dichroism spectrometer equipped with a Peltier temperature controller (Applied Photophysics., Ltd.). The spectra were recorded from 260 nm to 200 nm using a 2 mm path-length cuvette. Scans were repeated five times and averaged. The molar ellipticity was calculated per amino acid residue. Before measurement, 50 μM solutions of peptides with and without SWCNTs were incubated for 24 h in 150 mM KF, and another 50 μM peptide solution without SWCNTs were incubated for 24 h in distilled water.

Experimental Example 6

First, it was confirmed whether, like the linear block copolypeptide, the cyclic block copolypeptides can bind to and then solubilize SWCNTs. To this end, the peptide 1 of Synthesis Example 2 was used.

The arc-produced SWCNTs were suspended in tetrahydrofuran (THF) and equal amounts of the SWCNTs (5 μg) were added into microcentrifuge tubes. After THF evaporation, the solution (0.3 mL) of the cyclic block copolypeptide 1 of Synthesis Example 2 was added, and the mixture was subjected to sonication at room temperature for 15 min.

Figure 8:
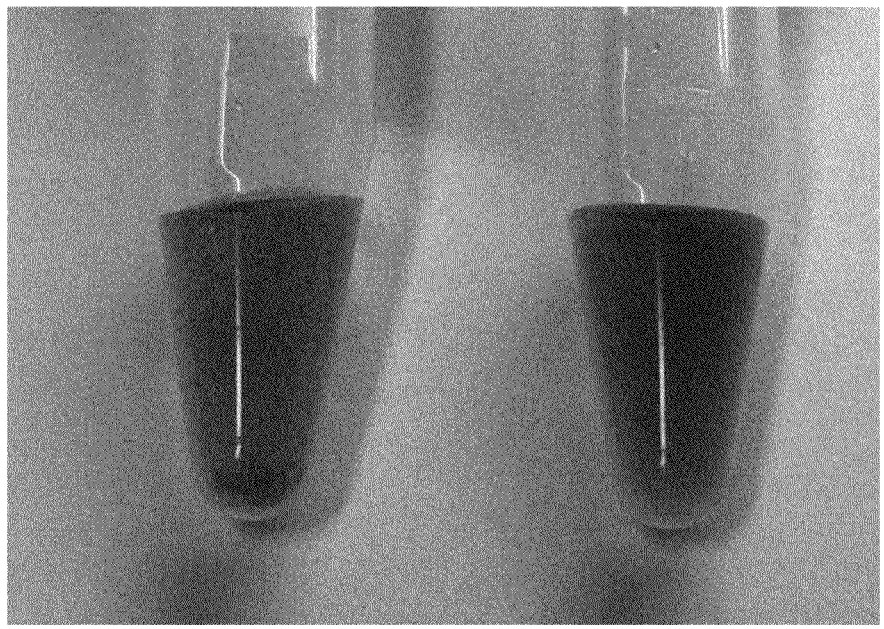
FIG. 8 shows images confirming whether SWCNTs were solubilized or not after bonding with cyclic block copolypeptides in a 20 mM aqueous salt solution (left) and a 150 mM aqueous salt solution after sonication (right).

As shown in FIG. 8 (left image), the SWCNTs were not effectively solubilized by peptide 1 in an aqueous solution of salt at a low concentration (20 mM). In contrast, most of the SWCNTs were suspended by peptide 1 in a 150 mM aqueous salt solution with the aid of sonication, as shown in FIG. 8 (right image). This result suggests that like the linear copolypeptide, the cyclic copolypeptide can also improve the solubility of the peptide/SWCNT hybrid at an appropriate ionic strength via hydrophobic and π-π stacking interactions of phenylalanine residues and interactions of the bioactive segments with the aqueous solution.

Experimental Example 7

Figure 9:
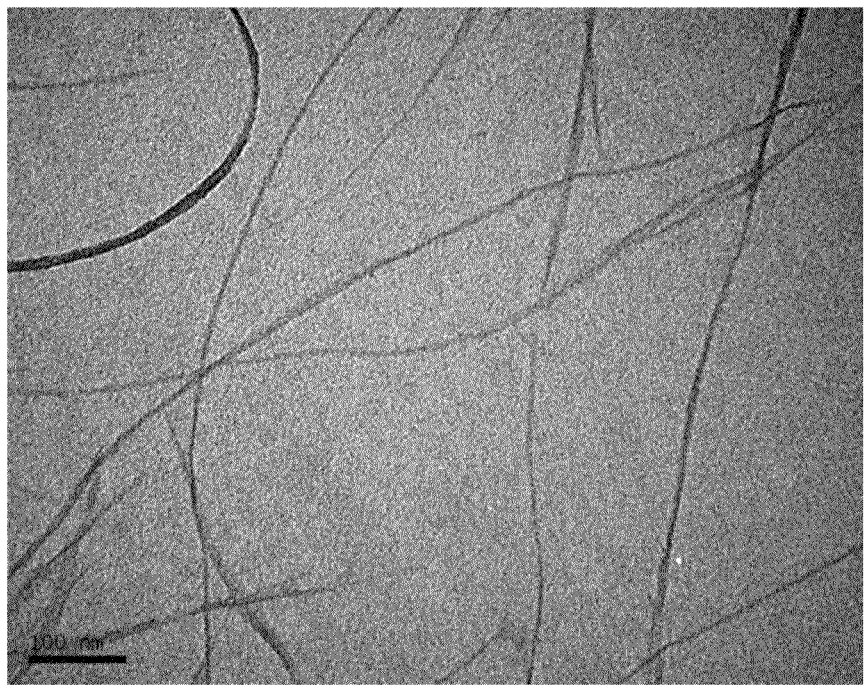
FIG. 9 is a TEM image of solubilized cyclic polypeptides/SWCNTs.

The TEM image of FIG. 9 clearly reveals that the cyclic copolypeptides solubilize the SWCNTs.

Experimental Example 8

CD spectra were measured to confirm the function of the peptide/SWCNT hybrids to stabilize the peptide α-helical structure.

Figure 10:
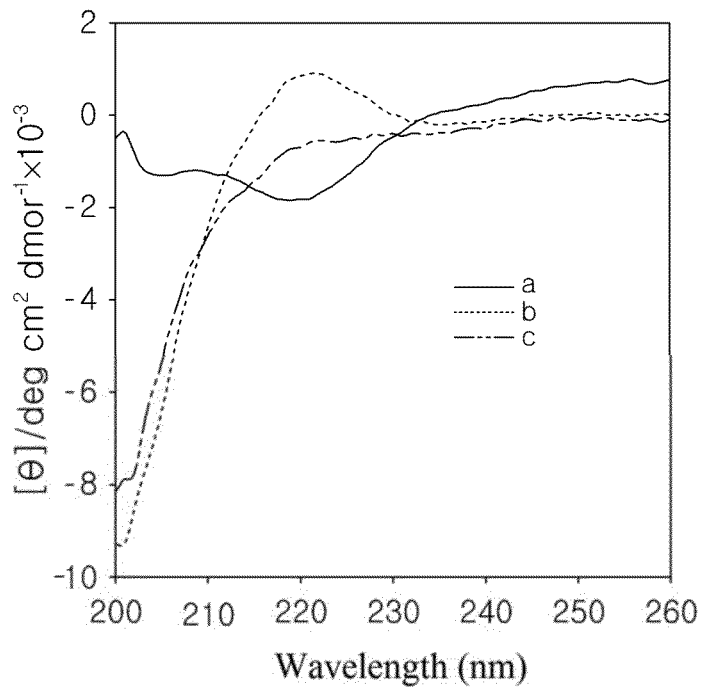
FIG. 10 shows CD spectra measured to confirm the function of cyclic polypeptide/SWCNT hybrids according to the present invention to stabilize the peptide α-helical structure.

In order to verify the function of SWCNTs as protein mimics supporting the α-helical structures, CD spectra were measured on a 50 μM solution of peptide 2 of Synthesis Example 2 in pure water and a solution of peptide 2 in a 150 mM aqueous salt solution (spectra b (dotted line) and c (alternate long and two short dashes line) of FIG. 10, respectively). Peptide 2 at a concentration of 50 μM was added to a 150 mM aqueous salt solution containing 20 μg of SWCNTs, followed by sonication to form peptide/SWCNT hybrids, which were used for CD spectrum measurement (spectrum a (solid line) of FIG. 10).

As shown in FIG. 10, the peptides without SWCNTs in water and the aqueous salt solution failed to stabilize the α-helical structures, but the CD spectrum of the peptide/SWCNT hybrids in the salt aqueous solution exhibited dramatic negative minimum values of ellipticity at 208 nm and 222 nm, revealing effective stabilization of the α-helical structure. From this result, it can be confirmed that SWCNTs strongly support the β-sheet forming segments of the cyclic copolypeptide via hydrophobic and π-π stacking interactions, demonstrating the ability of SWCNTs to stabilize the α-helical structure of the peptide, similarly giant proteins supporting α-helical structures in the body.

Experimental Example 9

In order to explore the possibility of using tryptophan residues except phenylalanine residues as β-sheet forming segments of the copolypeptides for the solubilization of SWCNTs, cyclic peptide 2 was applied to SWCNT solubilization.

Figure 11:
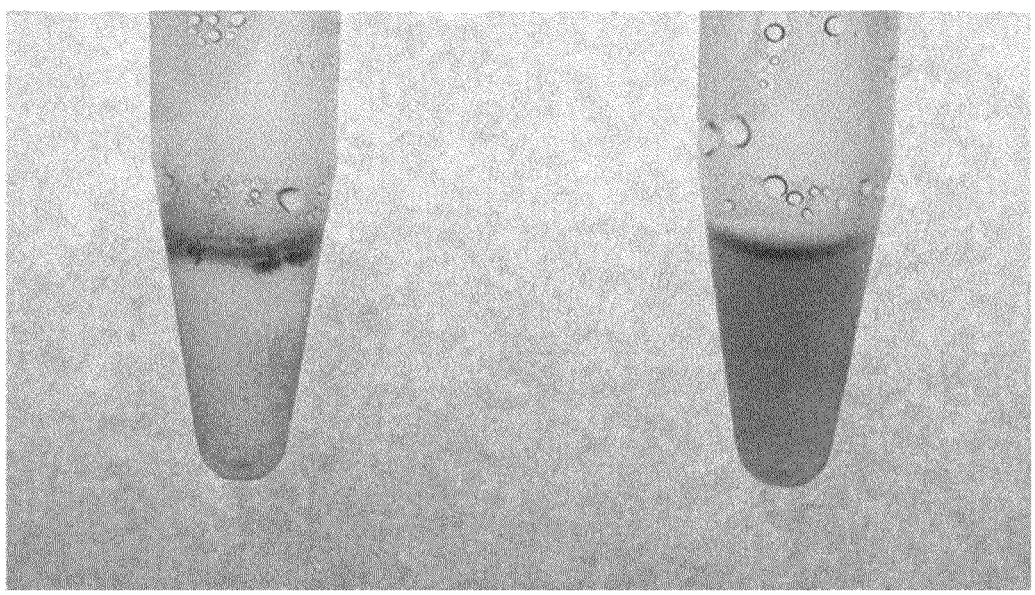
FIG. 11 shows images confirming the solubilization of SWCNTs using cyclic peptides in order to explore the possibility of using tryptophan residues except phenylalanine residues as β-sheet forming segments of copolypeptides for the solubilization of SWCNTs.

As shown in the left image of FIG. 11, SWCNTs were not effectively solubilized in a 150 mM aqueous salt solution containing no peptide. In contrast, most of the SWCNTs were suspended in a 150 mM KF salt solution containing peptide 1 at a concentration of 10 μM with the aid of sonication, as shown in the right image of FIG. 11. This result indicates that like phenylalanine residues, tryptophan residues can effectively solubilize SWCNTs via hydrophobic and π-π stacking interactions.

Experimental Example 10

An investigation was made as to whether cyclic peptides 3 and 4 of Synthesis Example 2 could solubilize SWCNTs despite variations in the number and arrangement of the β-sheet forming residues, particularly tryptophan residues, of the β-sheet polypeptide segments.

Figure 12:
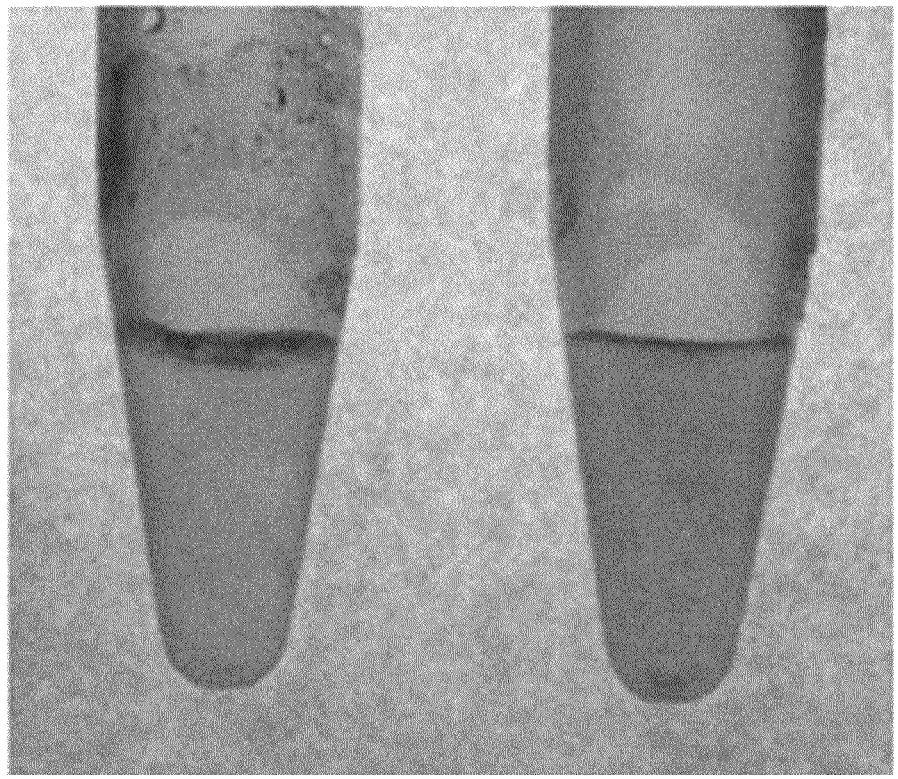
FIG. 12 shows images confirming the ability of peptides to solubilize SWCNTs despite variations in the number and arrangement of β-sheet forming residues, particularly, tryptophan residues, in β-sheet polypeptide segments.

As shown in FIG. 12, a 40 mM KF salt aqueous solution did not well suspend SWCNTs (left image), while a 40 mM salt aqueous solution containing 30 μM peptide 3 showed a tendency to solubilize SWCNTs with the aid of sonication (right image).

Taken together, the results of the foregoing experimental examples confirm that the cyclic peptides can be applied to the solubilization of SWCNTs so long as the kind, number and arrangement of the residues of the β-sheet polypeptide segments are appropriately varied.

INDUSTRIAL APPLICABILITY

As demonstrated above, several different association modes are present during the combination self-assembly process of the bioactive β-sheet block copolypeptides and CNTs. The bioactive β-sheet block copolypeptides can self-assemble, or can be used to functionalize the CNT hybrids depending on the situation. This is important in widening the potential applications of the bioactive β-sheet block copolypeptides. The bioactive β-sheet block copolypeptide/CNT hybrids can be utilized as stimuli-responsive biomaterials or to fabricate CNT-based electronic biosensor devices. In addition, the insight into the interactions between β-sheet peptides and carbon-based hydrophobic materials is expected to be useful in designing and developing inhibitors for protein-misfolding diseases.

The invention claimed is:

1. A hybrid of β-sheet block copolypeptides and carbon nanotubes
   wherein each (β-sheet block copolypeptide consists of a β-sheet polypeptide block and a bioactive polypeptide block,
   the β-sheet polypeptide block has an alternating series of nonpolar amino acids and polar amino acids or contains 50 to 100% of nonpolar amino acids,
   the bioactive polypeptide block consists of polar amino acids accounting for 50-100% of the total amino acids thereof,
   the β-sheet polypeptide block is non-covalently bound to the surface of the carbon nanotubes, and
   the bioactive polypeptide block is charged and exposed outside the hybrid;
   wherein the amino acids are the L-isomer form.

2. The hybrid of β-sheet block copolypeptides and carbon nanotubes according to claim 1, wherein the nonpolar amino acids are selected from phenylalanine, alanine, valine, isoleucine, leucine, methionine, tyrosine, and tryptophan, and the polar amino acids are selected from lysine, glycine, arginine, proline, glutamine, serine, histidine, aspartic acid, glutamic acid, threonine, aspargine, cysteine, and selenocysteine.

3. The hybrid of β-sheet block copolypeptides and carbon nanotubes according to claim 2, wherein the nonpolar amino acid of the β-sheet polypeptide block is phenylalanine or tryptophan, and the polar amino acid of the β-sheet polypeptide block is lysine, glutamic acid or glycine.

4. The hybrid of β-sheet block copolypeptides and carbon nanotubes according to claim 3, wherein the β-sheet polypeptide blocks self-assemble via β-sheet hydrogen bonds among the peptide strands, and the phenylalanine or tryptophan is non-covalently bound to the surface of the carbon nanotubes via π-π stacking and hydrophobic interactions.

5. The hybrid of β-sheet block copolypeptides and carbon nanotubes according to claim 1, wherein the β-sheet block copolypeptide is a macrocyclic peptide in which the N—and C-termini are linked to each other.

6. A biosensor comprising the hybrid of β-sheet block copolypeptides and carbon nanotubes according to any one of claims 1 to 5, and a ligand or receptor attached to the hybrid to react with a target biomaterial.

7. The biosensor according to claim 6, wherein the ligand or receptor is selected from enzyme substrates, ligands, amino acids, peptides, proteins, enzymes, lipids, cofactors, carbohydrates, and combinations thereof.

8. A composition comprising the hybrid of β-sheet block copolypeptides and carbon nanotubes of any of claims 1 to 5, wherein the hybrid is localized within the cytoplasm of a cell.

9. A method for preparing a hybrid of β-sheet block copolypeptides and carbon nanotubes, the method comprising (a) removing a suspending solvent from a suspension of carbon nanotubes to obtain pretreated carbon nanotubes, and (b) adding the pretreated carbon nanotubes to an aqueous solution of β-sheet block copolypeptides to obtain a dispersion, each β-sheet block copolypeptide consisting of a β-sheet polypeptide block and a bioactive polypeptide block, the β-sheet polypeptide block having an alternating series of nonpolar amino acids and polar amino acids or containing 50 to 100% of nonpolar amino acids, the bioactive polypeptide block consisting of polar amino acids accounting for 50-100% of the total amino acids thereof, the β-sheet polypeptide block is non-covalently bound to the surface of the carbon nanotubes and the amino acids are the L-isomer form.

10. The method according to claim 9, wherein the dispersion further comprises a salt.

11. The method according to claim 9 or 10, wherein, in step (a), the suspending solvent is tetrahydrofuran and is removed by centrifugation.

12. The method according to claim 10, wherein the salt is present at a concentration of 10 to 150 mM in the dispersion and the dispersion is prepared by sonication.

13. A method for internalizing peptides within the cytoplasm of a cell, the method comprising contacting a cell with a hybrid of β-sheet block copolypeptides and carbon nanotubes of any of claims 1 to 5, wherein the bioactive polypeptide component further comprises a cell-penetrating polypeptide.

14. The composition of claim 13, wherein the cell-penetrating polypeptide is a Tat cell-penetrating peptide.

15. The composition of claim 8, wherein the cell is a mammalian cell.

* * * * *